(12) United States Patent
Sutton

(10) Patent No.: US 9,354,216 B2
(45) Date of Patent: May 31, 2016

(54) INFRARED AERIAL THERMOGRAPHY FOR USE IN DETERMINING PLANT HEALTH

(71) Applicant: Brian Harold Sutton, Lowell, IN (US)

(72) Inventor: Brian Harold Sutton, Lowell, IN (US)

( * ) Notice: Subject to any disclaimer, the term of this patent is extended or adjusted under 35 U.S.C. 154(b) by 221 days.

(21) Appl. No.: 13/670,897

(22) Filed: Nov. 7, 2012

(65) Prior Publication Data

US 2013/0114641 A1 May 9, 2013

Related U.S. Application Data

(60) Provisional application No. 61/556,323, filed on Nov. 7, 2011.

(51) Int. Cl.
| | | |
|---|---|---|
| *G01J 5/00* | (2006.01) | |
| *G01N 33/00* | (2006.01) | |

(52) U.S. Cl.
CPC .................................. *G01N 33/0098* (2013.01)

(58) Field of Classification Search
USPC .......................................... 374/121, 124, 137
See application file for complete search history.

(56) References Cited

U.S. PATENT DOCUMENTS

| | | | | |
|---|---|---|---|---|
| 5,453,618 | A | * | 9/1995 | Sutton et al. ................... 250/334 |
| 5,637,871 | A | * | 6/1997 | Piety ........................ G01J 5/02 250/330 |
| 5,764,819 | A | * | 6/1998 | Orr et al. ........................ 382/110 |
| 5,878,356 | A | * | 3/1999 | Garrot et al. ...................... 701/1 |
| 6,212,824 | B1 | * | 4/2001 | Orr et al. ..................... 47/58.1 R |
| 6,597,991 | B1 | * | 7/2003 | Meron et al. ........................ 702/3 |
| 7,058,197 | B1 | * | 6/2006 | McGuire et al. .............. 382/100 |
| 7,184,859 | B2 | | 2/2007 | Hood et al. |
| 7,194,111 | B1 | | 3/2007 | Schaum et al. |
| 7,715,013 | B2 | | 5/2010 | Glaser et al. |
| 8,194,916 | B2 | | 6/2012 | Ma |
| 2004/0005085 | A1 | * | 1/2004 | Andersen ....................... 382/109 |
| 2004/0130714 | A1 | * | 7/2004 | Gellerman et al. ........... 356/300 |
| 2005/0149235 | A1 | * | 7/2005 | Seal et al. ...................... 700/283 |
| 2008/0112029 | A1 | * | 5/2008 | Bodkin ............................ 359/233 |
| 2008/0308732 | A1 | * | 12/2008 | Warnke et al. ................ 250/330 |
| 2009/0321644 | A1 | * | 12/2009 | Vogt .......................... G01J 5/06 250/338.4 |
| 2013/0308675 | A1 | * | 11/2013 | Sneed et al. .................... 374/121 |
| 2013/0325346 | A1 | * | 12/2013 | McPeek ............................ 702/2 |
| 2014/0098238 | A1 | * | 4/2014 | Boulanger et al. ............ 348/164 |
| 2015/0015697 | A1 | * | 1/2015 | Redden et al. .................. 348/89 |

OTHER PUBLICATIONS

Long wave definition, no. date.*

* cited by examiner

*Primary Examiner* — Mirellys Jagan
(74) *Attorney, Agent, or Firm* — Hartman Global IP Law; Gary M. Hartman; Michael D. Winter

(57) ABSTRACT

A method and system for monitoring the health of plants in a field. The method and system acquire a thermal image indicative of thermal energy emitted by the plants and process the thermal image to assess variations in the temperatures among the plants.

23 Claims, 1 Drawing Sheet

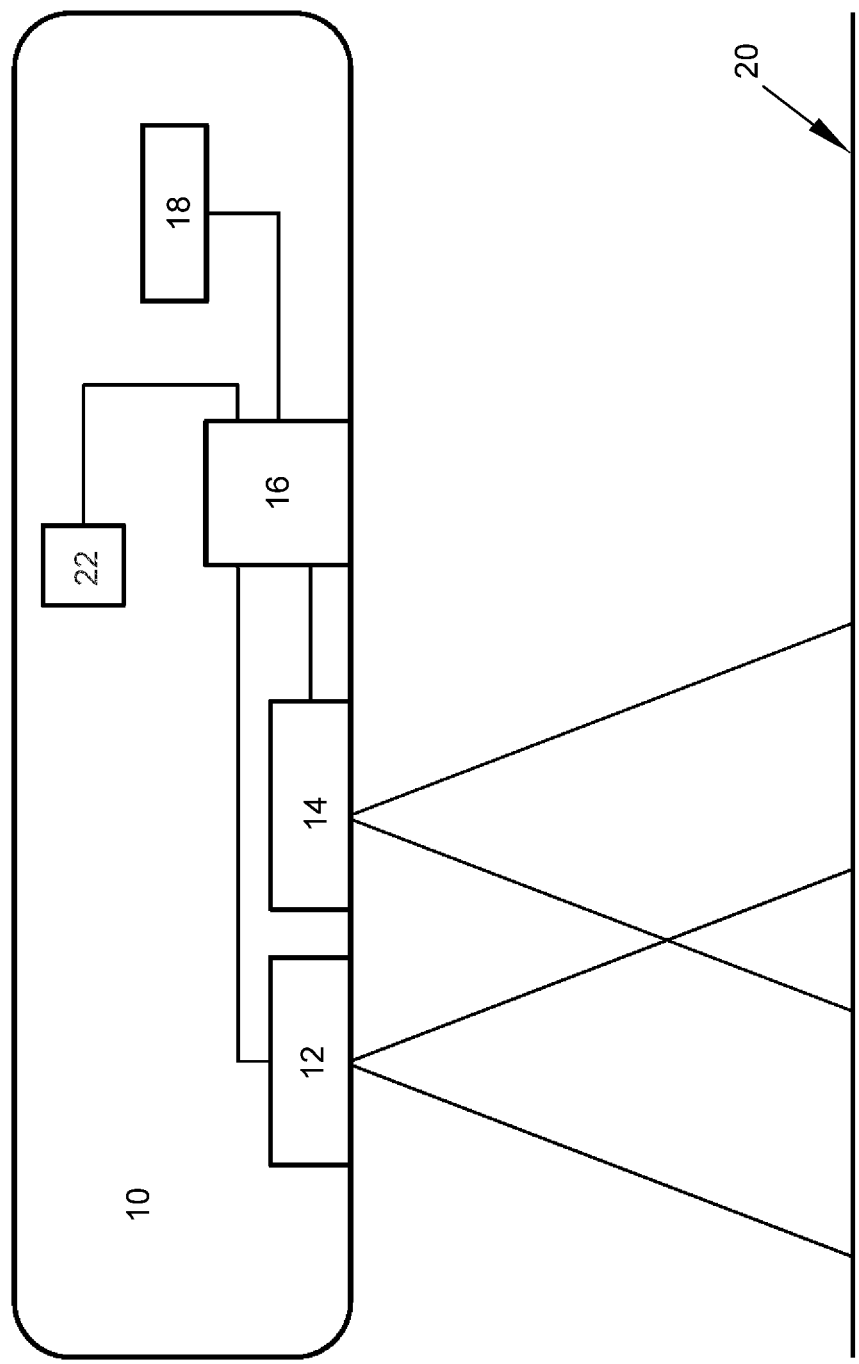

INFRARED AERIAL THERMOGRAPHY FOR USE IN DETERMINING PLANT HEALTH

CROSS REFERENCE TO RELATED APPLICATIONS

This application claims the benefit of U.S. Provisional Application No. 61/556,323, filed Nov. 7, 2011, the contents of which are incorporated herein by reference.

BACKGROUND OF THE INVENTION

The present invention generally relates to methods of monitoring the health of plants. More particularly, this invention relates to aerial imaging of vegetation to determine and monitor plant health.

Various technologies have been used in the past to measure temperature of plant leaves. For example, U.S. Pat. No. 7,058,197 uses visual light reflectance to generate NDVI images. This patent relies on reflected light from the sun, and therefore teaches that the optimum time for image acquisition using the disclosed process is within two hours of "solar noon" and on cloudless days. This makes it very impractical for a commercial application. In particular, this patent discloses > Aerial imagery was collected four times throughout the growing season. The image dates correlated with bare soil, VI2, VT, and R4 crop stages (see section on "Resolutions in Remote Sensing"). The aerial imagery was flown with digital cameras with an array size of approximately 1500 pixels wide and 1000 pixels in the along track dimension. The digital systems were 8-bit systems and were collected and stored on an on-board computer in a Tagged Image Format (TIF). Four bands were collected representing the blue, green, red, and near infrared portions of the electromagnetic spectrum (see section on "Spectral Nature of Remote Sensing"). The cameras were aligned in a two-by-two matrix and were rigid mounted (pseudo-bore sited) with the lenses focused [sic] on infinity. The imagery was flown at approximately 5000 feet above ground level (AGL) to produce a spatial resolution of approximately one meter by one meter (see section on "Resolutions in Remote Sensing"). The digital cameras have square pixels and are not interlaced during image acquisition. The optimum time for image acquisition was two hours before or two hours after solar noon (see section on "Resolutions in Remote Sensing"). Images were not acquired during times of poor atmospheric conditions (haze, rain, clouds). No cloud shadows were acceptable in the imagery.

In addition, it appears that the methodology disclosed by U.S. Pat. No. 7,058,197 is only able to indicate that a problem exists after a plant has actually changed its structure, as indicated by its color. In many cases, this is too late to take corrective action. Column 6 of U.S. Pat. No. 7,058,197 describes the extent of the methodology's capability as follows:

> The third major division of the electromagnetic spectrum ranges from around 1500 nanometers to approximately 3000 nanometers and is referred to as the middle-infrared. It is this portion of the electromagnetic spectrum where moisture plays a dominant role. Although other factors such as organic matter, iron content, and clay content have an effect, moisture appears be the primary mechanism affecting reflectance. More specifically, the higher the moisture content, the lower the reflectance. As objects lose moisture or begin to dry, their reflectance in this portion of the electromagnetic spectrum increases.

While this concept has been proven in a laboratory setting, applying this concept in practice has been somewhat evasive.

As another example, U.S. Pat. No. 6,597,991 uses thermal imaging to detect water content in leaves for irrigation purposes. This patent is reliant on obtaining actual temperatures and using ground-based references for calibration. Arguably, a significant disadvantage of U.S. Pat. No. 6,597,991 is its reliance on extremely accurate temperature measurements so that the need for irrigation can be determined. Such a requirement necessitates an extra step and additional costs associated with the calibration. U.S. Pat. No. 6,597,991 does not appear to contain a reference to the detection of disease in very early stages.

In view of the above, it can be appreciated that there are certain problems, shortcomings or disadvantages associated with the prior art, and that it would be desirable if an improved method were available for aerial monitoring of plant health that does not rely on sensing reflected light or ground-based measurements.

BRIEF DESCRIPTION OF THE INVENTION

The present invention provides a method and system suitable for aerial imaging of vegetation to determine and monitor plant health that does not rely on sensing reflected light or ground-based measurements.

According to a first aspect of the invention, a method of monitoring the health of plants in a field includes acquiring an aerial thermal image indicative of thermal energy emitted by the plants and processing the thermal image to assess variations in the temperatures among the plants.

According to a second aspect of the invention, a system for monitoring the health of plants in a field includes means for acquiring an aerial thermal image indicative of thermal energy emitted by the plants and means for processing the thermal image to assess variations in the temperatures among the plants.

A technical effect of the invention is the ability to monitor plant health with aerial imaging at any time without the need for ground-based measurements. In particular, it is believed that, by acquiring a thermal image indicative of thermal energy emitted by the plants and processing the thermal image to assess variations in the temperatures among the plants, a trained thermographer can detect disease or other stress factors in vegetation before they become apparent to visual or near infrared cameras.

Other aspects and advantages of this invention will be better appreciated from the following detailed description.

BRIEF DESCRIPTION OF THE DRAWINGS

FIG. 1 is a schematic plan representing an imaging system in accordance with an aspect of this invention.

DETAILED DESCRIPTION OF THE INVENTION

The present invention is generally applicable to imaging of plants utilizing energy (heat) emitted thereby. A particular aspect of the invention is based on a determination that by using certain microbolometer technology in a thermal imaging device, a trained thermographer can detect disease or other stress factors in vegetation before they become apparent to visual or near infrared cameras. While the invention is described as being suitable for monitoring plant health, other applications are foreseeable and therefore the present invention should not be limited to the described embodiments herein.

Preferred embodiments of the invention employ one or more high-resolution long-wave thermal imaging cameras 12 that can be mounted in an aircraft 10, as represented in FIG. 1, along with a digital camera 14, for example, a twenty-one megapixel digital camera, that can be used to provide a digital image for reference purposes. While the thermal imaging camera 12 and the digital camera 14 may be mounted to the aircraft 10 by any means, preferably the thermal imaging camera 12 and the digital camera 14 are mounted in a baggage compartment of the aircraft 10 and exposed through several holes in the aircraft skin beneath the baggage compartment in accordance with FAA AC43.13. Computer equipment 16 for controlling the thermal imaging camera 12 and the digital camera 14 may be located in the cockpit including a monitor 18 for the purpose of displaying and monitoring the thermal and/or digital camera images. However, alternative locations for the thermal imaging camera 12, the digital camera 14, and computer equipment 16 are foreseeable.

A thermal imaging camera 12 that has been used to carry out the invention is manufactured by Infrared Cameras, Inc., of Beaumont, Tex. USA. The model of the thermal imaging camera 12 is ICI 7640, equipped with a specially made 15 mm lens. The thermal imaging camera 12 produced an array of 480×640 pixels (currently considered to be high resolution, compared to thermal imaging cameras that offer resolutions of, for example, 320×240 pixels and 160×120 pixels) and used a microbolometer sensor that changes temperature as a result of being exposed to infrared (IR) energy (wavelengths between 0.7 and 300 micrometers). Images with resolutions lower than 480×640 pixels were found to be blurred when taken from high altitudes. Microbolometer sensors are considered to be "long wave" sensors because they collect light in wavelengths much longer than visible light, i.e., above the 0.4 to 0.7 micrometer spectral band. Wavelengths above visible light provide better penetration through smoke, smog, dust, and other interference that may be present under poor atmospheric conditions. Suitable microbolometer sensors preferably collect light in wavelengths of between about 7 and 14 micrometers. The microbolometer sensor that was utilized with the ICI 7640 camera is especially sensitive to thermal energy (infrared radiation) in the 7.5 to 13 micrometers range. Equipped with its sensor, the thermal imaging cameras 12 preferably utilized by the invention do not require reflected light from the sun, and therefore allow the system and method of this invention to be used under poor atmospheric conditions (haze, rain, clouds, etc.), and even in the darkness of night.

In contrast, U.S. Pat. No. 7,058,197 uses digital cameras that work primarily with reflected light in wavelengths of 0.38 to 0.72 micrometer to see plant color. These wavelengths are in the visible spectrum and require a light source from something above 6000° C., such as a light bulb filament or the sun. The white light from this energy source then bounces back (reflects) off objects in different wavelengths, enabling colors to be seen. Consequently, U.S. Pat. No. 7,058,197 teaches that the optimum time for image acquisition is two hours before or two hours after solar noon. In contrast, suitable cameras for use with the present invention do not require a source of high energy because they measure energy that is emitted, not reflected, by plants.

Because the thermal imaging camera 12 suitable for use with this invention detects energy waves of much longer wavelengths, (e.g., 7 to 14 micrometers), the thermal imaging camera 12 is able to detect objects over a range of temperatures, for example, about −35° C. to about 200° C. A computer program can be used to focus the thermal imaging camera's sensitivity onto an area that encompasses a range of temperatures above and below the ambient temperature of the crop canopy, for example, about 10° C. above and below. A color palette can then be used in the computer program to build an image showing the relative temperature of the canopy. Such a computer program is well within the capabilities of those skilled in the relevant art, and therefore will not be discussed in any detail here.

In the above manner, the invention can be performed to evaluate plants under poor atmospheric conditions and even in total darkness and measure plant health based on temperature, without the need for using reflected light as proposed by U.S. Pat. No. 7,058,197. The invention can employ a technique by which the computer program is written to be further able to compensate for clouds if the images are taken during daylight hours. This can be accomplished by utilizing the aforementioned separate digital camera 14, whose digital images can overlay thermal images acquired with the thermal imaging camera 12. Since clouds are readily apparent in the digital image of the digital camera 14, the computer program can be used to compensate for cooler areas that exist beneath clouds.

At the time of the invention, thermal imaging cameras 12 of the type used by the invention were believed to be limited to one camera mounted on NASA's Space Shuttle and another leased to the University of Washington for environmental research. Up until the time of the invention, it was believed that there were no uncooled microbolometer thermal imaging cameras 12 commercially available with resolutions suitable for use with the present invention. This camera technology was previously developed for the U.S. military as the heat-seeking element in Tomahawk missiles, and has recently been made available to the general public. While thermal imaging cameras have been available for many years prior to the time of the invention, they were required to be cooled with liquid nitrogen and therefor impractical for use in most aircraft for safety and economic reasons.

Through the use of this thermal imaging camera 12 and analytical software, a trained thermographer can see very subtle differences in canopy temperature. In fact, the thermal imaging camera 12 manufactured by Infrared Cameras, Inc., is believed to be capable of measuring differences of as little as 0.03° C. Through careful analysis of the thermal images, these subtle differences in temperature can guide a user on the ground to suspect areas in a field.

The invention encompasses various modifications and improvements to the system, including but not limited to assisting ground inspection of the fields. For example, a tracking device 22, such as a G.P.S. device, located within or on the aircraft 10 may be used to log the position of the aircraft 10 on timed intervals, such as once per second, in addition to storing the compass heading of the aircraft 10. Computer software can then be used to synchronize this information with the time at which each individual image is taken. The software may then orient all of the images in a "north up" for easier referencing during ground inspection regardless of the flight path of the aircraft 10.

The information recorded by the tracking device 22 may further be used with computer software to geo-locate all of the images and sort them into groups for each individual tract of land, for example a farm. Preferably, the software superimposes each image on a geographical map at the corresponding location where the image was taken. In addition to improving ground inspections, this data may be used to compile a database of images sorted according to each individual farm.

Preferably, the database comprises names for the fields and their corresponding coordinates. This allows the software to not only superimpose the image on a geographical map at its corresponding location but also to provide the name of the field captured in the image. For example, the image may be superimposed on a geographical map with a label comprising the name of the client, farm, and specific field represented in the image.

Ground inspections can further be improved by providing the user with access to this database of images during the physical ground inspection. This may be accomplished by geo-referencing the image with a mobile device, for example a tablet computer with software written specifically for this purpose. Preferably, the software is adapted to automatically download each image associated with a particular parcel or client, for example using a File Transfer Protocol (FTP) method, and allow viewing of all the associated images. The user can then choose to load any image to the overlay map and manually manipulate the image to align field boundaries. Preferably, the software is adapted to allow the user to adjust the color tone and transparency of the image for viewing purposes. The user can then walk through the field with the user's present location shown on top of the thermal or digital image, allowing the ability to precisely navigate to the areas of most interest. The user can then gather samples and determine the cause of the anomaly in question. If this invention is used for analyzing a farm, timeliness of the ground inspection of the plants is critical for the farmer to make important management decisions. Therefore, quick access to the images is a particularly advantageous aspect of the process and system.

The importance of the technology provided by the present invention cannot be overstated due to recent developments in agricultural practices. Chemical supply companies have released fungicides products onto the market to combat many diseases of nearly all commercially grown crops. These fungicides have proven to provide such an economic advantage that many farmers have preemptively contracted this service to be sprayed from airplanes using a "blanket coverage" technique, and therefore even in areas where disease is not present. Though this may be considered "insurance" and potentially beneficial, in many instances it may not. With the process of the present invention, crop health can be monitored to enable a farmer to react in sufficient time to mitigate damage in the event that a crop becomes infested. This is enormously beneficial from an economic standpoint, and quite possibly from an environmental standpoint.

Though U.S. Pat. No. 7,058,197 broaches certain aspects of the present invention, the method and system described herein rely on wavelengths in the range of about 7 to 14 micrometers, which is a different region of the electromagnetic spectrum. U.S. Pat. No. 7,058,197 appears to make an assumption that moisture is the primary mechanism affecting reflectance, more specifically, higher moisture contents correspond to lower reflectance. Though not wishing to be held to any particular theory, the present invention recognizes the significance of radiated energy, in other words, warmer surfaces emit more energy, and that moisture is simply a medium that promotes energy absorption as opposed to energy emittance. It also appears to be evident that U.S. Pat. No. 7,058,197 relies on reflected light energy, whereas the process and system of the present invention do not require light, but simply measure infrared radiation from the target body.

The process of the present invention also does not require a calibration procedure of the type required by U.S. Pat. No. 6,597,991, and is more driven by relativity. Therefore, ground-based measurements are not required for the present invention.

While the invention has been described in reference to the use of particular equipment and technologies, it should be apparent that other forms could be adopted by those skilled in the art. For example, improved technologies could provide greater resolution of the thermographic image. Furthermore, it is foreseeable that infrared images could be acquired with satellite cameras, though as yet resolution is believed to be inadequate for use with the present invention due to atmospheric attenuation. Therefore, the scope of the invention is to be limited only by the following claims.

The invention claimed is:

1. A method of monitoring the health of plants in a field, the method comprising:
    acquiring an aerial thermal image of at least a portion of the field that is indicative of thermal energy emitted by the plants within the portion, the thermal image being acquired from an aircraft as the aircraft flies over the field, the thermal image having a resolution of at least 480×640 pixels;
    processing the thermal image to assess variations in temperatures among the plants from which disease is detected in the plants;
    mapping the location of the thermal image to a position on a geographical map;
    overlaying the thermal image on the geographical map;
    providing the thermal image on the geographical map to a user in the field; and
    locating and displaying the user's present location on the thermal image on the geographical map and thereby enabling the user to navigate to areas in the field.

2. The method of claim 1, wherein the thermal image is acquired by measuring infrared radiation emittance of the plants, and the measured infrared radiation emittance is in the range of about 7 to 14 micrometers.

3. The method of claim 1, wherein the variations in temperature among the plants are detected before becoming apparent with visual and near infrared cameras.

4. The method of claim 1, further comprising positioning a thermal imaging system in the aircraft prior to acquiring the thermal image, wherein the thermal image is acquired with the thermal imaging system while the aircraft is in flight.

5. The method of claim 4, further comprising tracking and synchronizing the position and heading of the aircraft to the thermal image to orient the thermal image.

6. The method of claim 4, further comprising:
    tracking a position of the aircraft with a tracking device;
    tracking a heading of the aircraft with a compass;
    logging the position and heading of the aircraft when the thermal image is acquired; and
    orienting the thermal image based on the position and heading of the aircraft when the thermal image was acquired.

7. The method of claim 4, further comprising:
    mapping the location of the thermal image to a position on the geographical map;
    overlaying the thermal image on the geographical map; and
    adjusting the color tone or transparency of the thermal image.

8. A method of monitoring the health of plants in a field, the method comprising:
    positioning a thermal imaging system in an aircraft;
    acquiring an aerial thermal image of at least a portion of the field that is indicative of thermal energy emitted by the plants within the portion, the thermal image being acquired with the thermal imaging system from the aircraft as the aircraft is in flight and flies over the field, the thermal image having a resolution of at least 480×640 pixels;

processing the thermal image to assess variations in temperatures among the plants from which disease is detected in the plants;

obtaining a digital image of the portion of the field;

overlaying the thermal and digital images; and compensating for cooler areas that exist within the portion of the field as a result of cloud coverage detected in the digital image.

9. A method of monitoring the health of plants in a field, the method comprising:

acquiring an aerial thermal image of at least a portion of the field that is indicative of thermal energy emitted by the plants within the portion, the thermal image being acquired from an aircraft as the aircraft flies over the field, the thermal image having a resolution of at least 480×640 pixels;

processing the thermal image to assess variations in temperatures among the plants from which disease is detected in the plants;

mapping the location of the thermal image to a position on a geographical map;

overlaying the thermal image on the geographical map; and adjusting the color tone or transparency of the thermal image.

10. The method of claim 9, further comprising:

providing the thermal image on the geographical map to a user in the field; and locating and displaying the user's present location on the thermal image on the geographical map and thereby enabling the user to navigate to areas in the field.

11. A method of monitoring the health of plants in a field, the method comprising:

positioning a thermal imaging system in an aircraft;

acquiring an aerial thermal image of at least a portion of the field that is indicative of thermal energy emitted by the plants within the portion, the thermal image being acquired with the thermal imaging system from the aircraft as the aircraft is in flight and flies over the field, the thermal image having a resolution of at least 480×640 pixels;

processing the thermal image to assess variations in temperatures among the plants from which disease is detected in the plants;

tracking a position of the aircraft with a tracking device;

logging the position of the aircraft when the thermal image is acquired;

storing the thermal image in a database comprising a plurality of images;

labeling the thermal image within the database with the name of the field captured in the thermal image by comparing the position of the aircraft that was logged when the thermal image was acquired with names of fields and their corresponding coordinates stored in the database; and sorting the thermal image relative to the plurality of images based on the labeling.

12. A system for monitoring the health of plants in a field, the system comprising:

means for acquiring an aerial thermal image of at least a portion of the field that is indicative of thermal energy emitted by the plants within the portion and being configured to measure variations in temperature as little as 0.03° C., the thermal image being acquired from an aircraft as the aircraft flies over the field, the thermal image having a resolution of at least 480×640 pixels;

means for obtaining a digital image of the portion of the field; and means for compensating for cooler areas that exist within the portion of the field as a result of cloud coverage detected in the digital image.

13. The system of claim 12, wherein the acquiring means measures infrared radiation emittance of the plants, and the measured infrared radiation emittance is in the range of about 7 to 14 micrometers.

14. The system of claim 12, wherein the variations in temperature among the plants are detected before becoming apparent with visual and near infrared cameras.

15. The system of claim 12, wherein the acquiring means comprises a thermal imaging system and a microbolometer.

16. The system of claim 12, wherein the acquiring means comprises a high-resolution long-wave thermal imaging camera and a digital camera.

17. The system of claim 12, wherein the acquiring means is adapted to acquire the thermal image at night or under poor atmospheric conditions.

18. The system of claim 12, further comprising:

means for mapping the location of the thermal image to a position on a geographical map;

means for overlaying the thermal image on the geographical map; and means for adjusting the color tone or transparency of the thermal image.

19. The system of claim 12, further comprising means for tracking the position and heading of the aircraft and means for synchronizing the position and heading to the thermal image to orient the thermal image.

20. The system of claim 19, wherein the tracking means comprises a G.P.S. tracking device and a compass, and the synchronizing means orients the thermal image using the position and heading of the aircraft when the thermal image was acquired.

21. A method of monitoring the health of plants in a field using the system of claim 12, the method comprising:

acquiring a thermal image of at least a portion of the field that is indicative of thermal energy emitted by the plants within the portion; and processing the thermal image to assess variations in temperatures among the plants from which disease is detected in the plants.

22. A system for monitoring the health of plants in a field, the system comprising:

means for acquiring an aerial thermal image of at least a portion of the field that is indicative of thermal energy emitted by the plants within the portion and being configured to measure variations in temperature as little as 0.03° C., the thermal image being acquired from an aircraft as the aircraft flies over the field, the thermal image having a resolution of at least 480×640 pixels;

means for mapping the location of the thermal image to a position or a geographical map;

means for overlaying the thermal image on the geographical map;

means for adjusting the color tone or transparency of the thermal image; and means for providing the thermal image mapped to the geographical map to a mobile handheld device, and the handheld device is configured to locate and display a position of the handheld device on the thermal image during physical ground inspections of the plants in the field.

23. A system for monitoring the health of plants in a field, the system comprising:
- means for acquiring an aerial thermal image of at least a portion of the field that is indicative of thermal energy emitted by the plants within the portion and being configured to measure variations in temperature as little as 0.03° C., the thermal image being acquired from an aircraft as the aircraft flies over the field, the thermal image having a resolution of at least 480×640 pixels;
- means for tracking the position and heading of the aircraft and means for synchronizing the position and heading to the thermal image to orient the thermal image;
- means for storing the thermal image in a database comprising a plurality of images;
- means for labeling the thermal image with the name of the field captured in the thermal image by comparing the position of the aircraft when the thermal image was acquired with names of fields and their corresponding coordinates stored in the database; and
- means for sorting the thermal image relative to the plurality of images based on the labeling.

* * * * *